United States Patent
Tallman et al.

(10) Patent No.: US 12,213,865 B2
(45) Date of Patent: *Feb. 4, 2025

(54) ABSORBENT ARTICLE WITH ABSORBENT STRIPS

(71) Applicant: Medline Industries, LP, Northfield, IL (US)

(72) Inventors: Amanda Tallman, Kenosha, WI (US); Stephen Kaidantsis, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 312 days.

This patent is subject to a terminal disclaimer.

(21) Appl. No.: 17/743,838

(22) Filed: May 13, 2022

(65) Prior Publication Data

US 2022/0323268 A1    Oct. 13, 2022

Related U.S. Application Data

(63) Continuation of application No. 16/117,077, filed on Aug. 30, 2018, now Pat. No. 11,351,069.

(51) Int. Cl.
*A61F 13/494* (2006.01)
*A61F 13/534* (2006.01)
*A61F 13/53* (2006.01)

(52) U.S. Cl.
CPC .... *A61F 13/49473* (2013.01); *A61F 13/4946* (2013.01); *A61F 13/534* (2013.01); *A61F 2013/530007* (2013.01); *A61F 2013/530489* (2013.01)

(58) Field of Classification Search
CPC .. A61F 2013/49486; A61F 2013/49493; A61F 13/4946; A61F 13/4757; A61F 2013/530007; A61F 13/49473; A61F 13/49453; A61F 2013/49069
See application file for complete search history.

(56) References Cited

U.S. PATENT DOCUMENTS

| | | | | |
|---|---|---|---|---|
| 4,657,539 A | * | 4/1987 | Hasse | A61F 13/49426 604/385.25 |
| 5,676,661 A | * | 10/1997 | Faulks | A61F 13/495 604/385.21 |
| 5,853,405 A | | 12/1998 | Suprise | |
| 6,060,638 A | | 5/2000 | Paul et al. | |

(Continued)

OTHER PUBLICATIONS

The Extended European Search Report; International Application No. PCT/US2019/048806; Medline Industries, Inc. (Tallman, et al.); Apr. 14, 2022.

(Continued)

*Primary Examiner* — Susan S Su
(74) *Attorney, Agent, or Firm* — SandBright, PLLC; Robert Dan Spendlove

(57) ABSTRACT

An absorbent article, a portion of which is configured to absorb fluids, has a chassis with a length greater than its width. The chassis length extends in a longitudinal direction from the back to the front of a user between first and second longitudinal edges and the width extends in a lateral direction substantially perpendicular to the length and between first and second lateral edges. Absorbent strips with a length greater than their width are arranged at outer edges of the chassis for added absorbency of the article.

16 Claims, 8 Drawing Sheets

(56) References Cited

U.S. PATENT DOCUMENTS

| | | |
|---|---|---|
| 6,244,216 B1 | 6/2001 | Ochi |
| 6,613,955 B1 | 9/2003 | Lindsay et al. |
| 6,652,497 B1 | 11/2003 | Suprise |
| 8,388,589 B2 | 3/2013 | Kaneko et al. |
| 2003/0187417 A1 | 10/2003 | Kudo et al. |
| 2005/0143703 A1 | 6/2005 | Persson |
| 2005/0182381 A1 | 8/2005 | Suzuki et al. |
| 2006/0224138 A1 | 10/2006 | Heki et al. |
| 2014/0171898 A1 | 6/2014 | Greening et al. |
| 2015/0374568 A1 | 12/2015 | Miralles et al. |
| 2016/0074242 A1 | 3/2016 | Toro et al. |
| 2017/0172818 A1 | 6/2017 | Suzuki |

OTHER PUBLICATIONS

Notification of Transmittal of the International Search Report and the Written Opinion of the International Searching Authority, or the Declaration; International Application No. PCT/US2019/048806; Medline Industries, Inc. (Tallman, et al.); Dec. 11, 2019.

International Search Report; International Application No. PCT/US2019/048806; Medline Industries, Inc. (Tallman, et al.); Dec. 11, 2019.

\* cited by examiner

ABSORBENT ARTICLE WITH ABSORBENT STRIPS

RELATED APPLICATIONS

This application is a continuation of U.S. patent application Ser. No. 16/117,077, filed on Aug. 30, 2018, which is incorporated herein by reference.

FIELD OF THE INVENTION

The present invention relates generally to absorbent articles and, in particular, to the use of absorbent strips with the article.

BACKGROUND

Millions of people of all ages suffer from incontinence of the bowel or bladder. Whether an infant, adult, or elderly person, the underlying cause of incontinence varies but the method of treatment typically involves absorbent article products. Adult incontinent briefs, disposable diapers, pull-up diapers, protective underwear and underpads can alleviate some of the emotional and physical discomfort of incontinence by absorbing and containing liquid and other discharges from the human body to prevent body and clothing soiling.

Typical absorbent articles include a topsheet facing the wearer that permits fluid exudates to pass through and a backsheet that prevents the exudates from escaping from the absorbent article. Much advancement has been made in the art since the introduction of the disposable absorbent article. However, quality care for patients and other users of absorbent articles requires that the article be capable of withstanding a considerable amount of liquid and other discharge. Most articles, though adapted to retain a heavy amount of liquid and other discharges, fall short of providing adequate collection and retention in all instances.

From time-to-time the absorbent articles known in the art, like those described above, fail in their ability to retain and keep liquid and other discharge from exiting the sides or front of the diaper. Such instances are known in the industry and are often referred to as a "blow out." Failure in waste retention is uncomfortable and bothersome to the user, but more so, is embarrassing and can result in unwanted attention, especially for users who are insecure about having to use the article. Accordingly, there is a need to provide an absorbent article that can better retain fluids and other discharge deposited onto the article to prevent such blow-outs from occurring.

BRIEF DESCRIPTION OF THE DRAWINGS

Advantages of the invention will become apparent upon reading the following detailed description and upon reference to the drawings.

Figure 1:
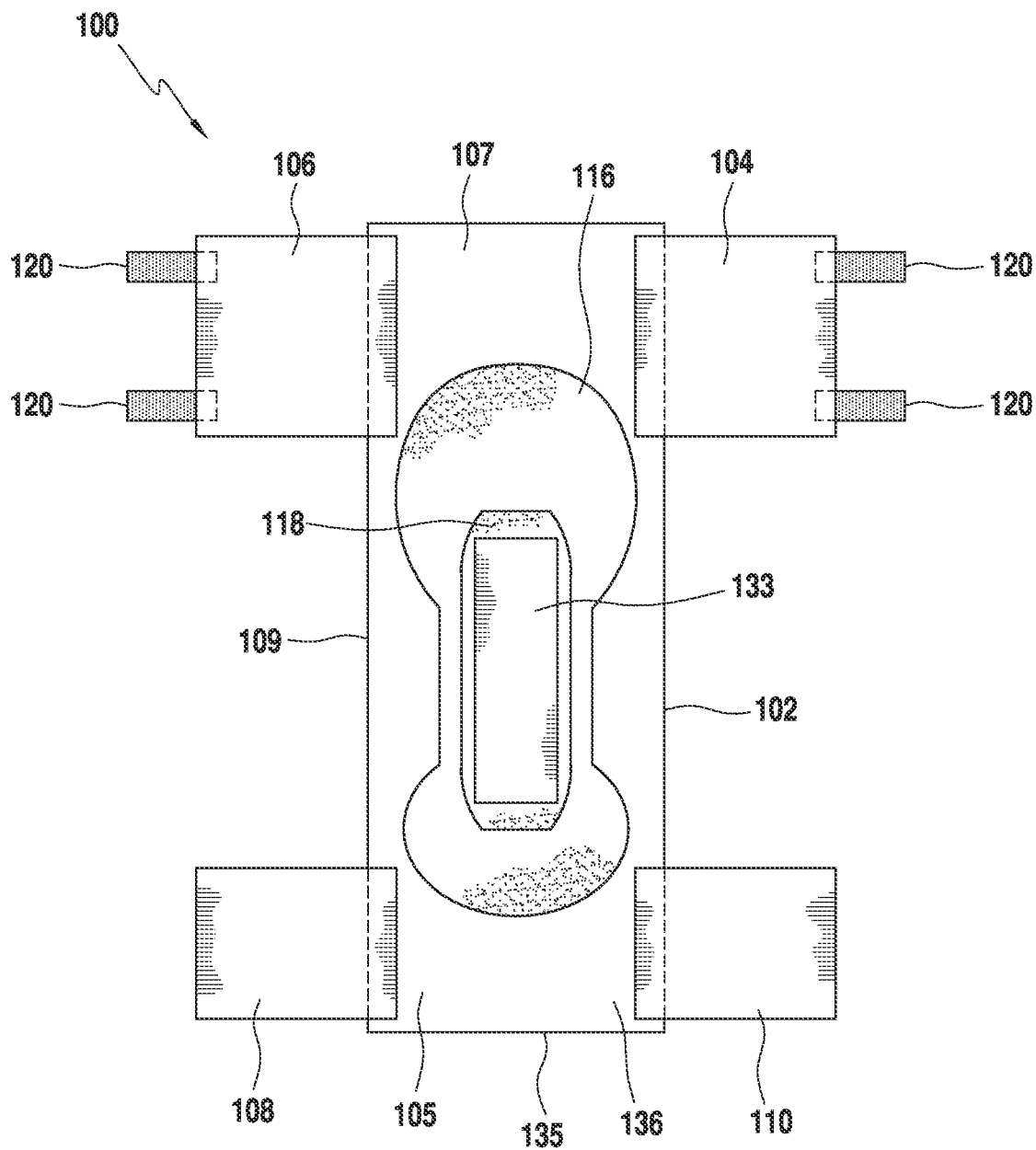
FIG. 1 is a top plan view of an absorbent article in a substantially flat un-contracted position according to the prior art.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, and the like may be used solely to distinguish one entity or action from another entity or action without necessarily requiring or implying any actual such relationship, direction or order between such entities or actions.

Absorbent articles as described herein generally include a moisture-pervious inner layer, an absorbent layer, and a moisture-impervious outer layer. Although the remainder of the description will be specifically directed to adult incontinence articles, such as disposable diapers, it is to be understood that the embodiments may also be implemented using other absorbent articles and that the properties and uses described below apply to these other absorbent articles as well. Throughout this application, the terms absorbent article and diaper are used interchangeably. However, it should be understood that the term diaper is intended to include other absorbent articles, such as training pants, incontinence pads, etc., as would be understood by one of ordinary skill in the art. The terms user and patient are also used interchangeably to indicate a person on whom a diaper is placed.

Figure 2:
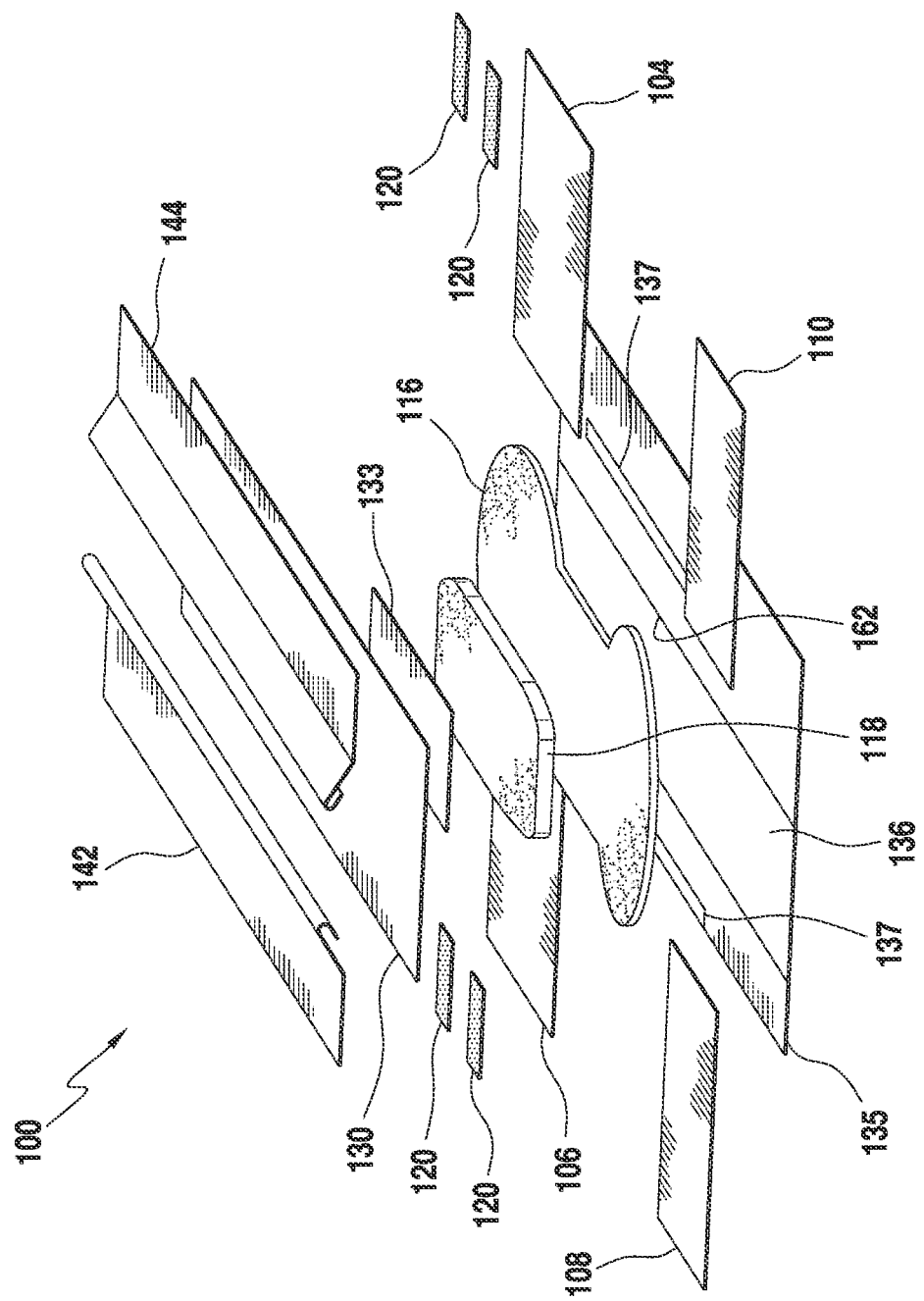
FIG. 2 is an exploded perspective view of the absorbent article of FIG. 1, again in a substantially flat un-contracted position.

FIGS. 1 and 2 illustrate an exemplary non-limiting general embodiment of an absorbent article 100 known in the art. FIG. 1 illustrates a plan view of the absorbent article 100 in a substantially flat un-contracted state. As shown in these figures, the absorbent article 100 generally consists of several layers, including an inner layer, an absorbent layer, and an outer layer. The inner layer faces a wearer and contacts the skin of the wearer when the absorbent article 100 is secured to the wearer. The inner layer may comprise a topsheet 130 that is composed of a moisture-pervious fabric suitable to allow bodily discharge to pass through the inner layer and be absorbed by the absorbent layer. Non-limiting examples of materials suitable to form the topsheet 130 include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon-based chemicals.

The plan view of FIG. 1 is shown from the top or patient contacting side of the absorbent article. The topsheet (130) and other components have been removed for clarity. FIG. 2 is an exploded perspective view of the absorbent article 100. Again, the article 100 is shown in a substantially flat un-contracted state with certain items removed for clarity.

As shown in FIG. 1, an embodiment of the absorbent article 100 comprises a chassis 102. The chassis 102 includes a front waist region 105, a back waist region 107, and a crotch region 109 that is disposed longitudinally between the front and back waist regions 105 and 107. The front waist region 105 and the back waist region 107 generally comprise those portions of the absorbent article 100 which, when worn, encircle the waist of the wearer. The crotch region 109 is that portion of the absorbent article 100 which, when the absorbent article 100 is worn, is generally positioned between the legs of the wearer.

The chassis 102 has a shape such that its outer perimeter is rectangular or at least substantially rectangular in the illustrative embodiment of the absorbent article 100. In other embodiments, there may be portions of the chassis that are shaped and/or removed, such as in the crotch region 109, for example, resulting in a narrower crotch region portion 109 to provide a contoured fit between the legs. Still other embodiments known in the art have different shaped chassis, such as hourglass shapes, T-shapes, and the like.

Rear side panels 104, 106 are coupled to and may extend from the back waist region 105. The disposable article may further include front side panels 108, 110 that are coupled to and may extend from the front waist region 105. The back region 107 is generally positioned against the back of the user. The front region 105 is generally positioned against the front of the user. The rear side panels 104, 106 are configured to wrap around a wearer's waist from back to front, extending from each side of the back waist region 105. The front side panels 108, 110 are configured to wrap around a wearer's waist from front to back. In this manner, rear side panel 106 can be connected to front side panel 108 and rear side panel 104 can be connected to front side panel 110 to couple the front region 105 to the back region 107. In this embodiment there are four side panels 104, 106, 108, 110. However, other embodiments known in the art may be configured with more or fewer side panels. For instance, rear side panels 104, 106 may connect directly to an outside surface of front waist region 105 rather than to front side panels 108, 110.

The side panels may attach to the chassis 102 in a variety of manners as would be apparent to one of skill in the art. Alternatively, one or more of the side panels may be integrally formed, in whole or in part, with a backsheet 135 or topsheet 130 of the absorbent article. The backsheet 135 will have an outside surface 134 facing away from the patient wearing the absorbent article and an inside surface 136 facing toward the patient.

The rear side panels 104, 106 may also include fasteners 120. Fasteners 120 may comprise adhesive tape, hook and loop, snaps or any other appropriate fasteners as would be understood by one of ordinary skill in the art. As shown in the illustrative embodiment, rear side panel 104, 106 includes two fasteners 120. Fasteners 120 can be configured to operatively couple rear side panels 104, 106 to a front region 105 of the diaper chassis 102. Alternative, fasteners 120 may also engage front side panels 108, 110 to attach rear side panels 104, 106, respectively. While FIG. 1 depicts rear side panels 104, 106 as including two fasteners 120, it will be understood to those skilled in the art that more or fewer fasteners may be used. While FIG. 1 depicts fasteners 120 sized and shaped a particular way, in other embodiments, fasteners 120 can be a different size and/or shape. Alternatively, the front side panels 108, 110 may include fasteners in additions to, or in place of, the fasteners 120 attached to rear side panels 104, 106.

In another embodiment, the front region 105 and/or front panels 108, 110 may include added or modified features to reinforce or increase the affinity to the fastening device. Additionally, features may be employed to allow adhesive fasteners to be attached and detached from the fastening region multiple times. Those skilled in the art will recognize that there are multiple approaches to doing so via modification of the base material as well as additions of various materials. For example, fasteners 120 may incorporate the hook component of a hook-and-loop closure and portions of the front region 105 and/or front panels 108, 110 may be comprise a corresponding loop component. The surface of front region 105 and/or front panels 108, 110 may be treated to increase or decrease the affinity for the hook components. Alternatively, separate loop component material may be adhered to the surface of the front region 105 and/or front panels 108, 110.

Referring again to FIGS. 1 and 2, embodiments of the absorbent article 100 include an absorbent layer. The absorbent layer may comprise an acquisition and/or distribution ("A/D") layer 133, a first absorbent core 116, and a second absorbent core 118.

The liquid acquisition and/or distribution layers serves to rapidly acquire and then distribute acquired liquid to an absorbent core for retention. To achieve rapid acquisition and distribution, these layers often include cellulosic fibers. These layers can include cross-linked cellulosic fibers to impart bulk and resilience to the layer, and wood pulp fibers to increase the wicking of liquid within the layer and to facilitate distribution of the liquid throughout the layer and ultimately to another layer, such as a storage layer, that is in liquid communication with the distribution layer.

Figures 3, 4:
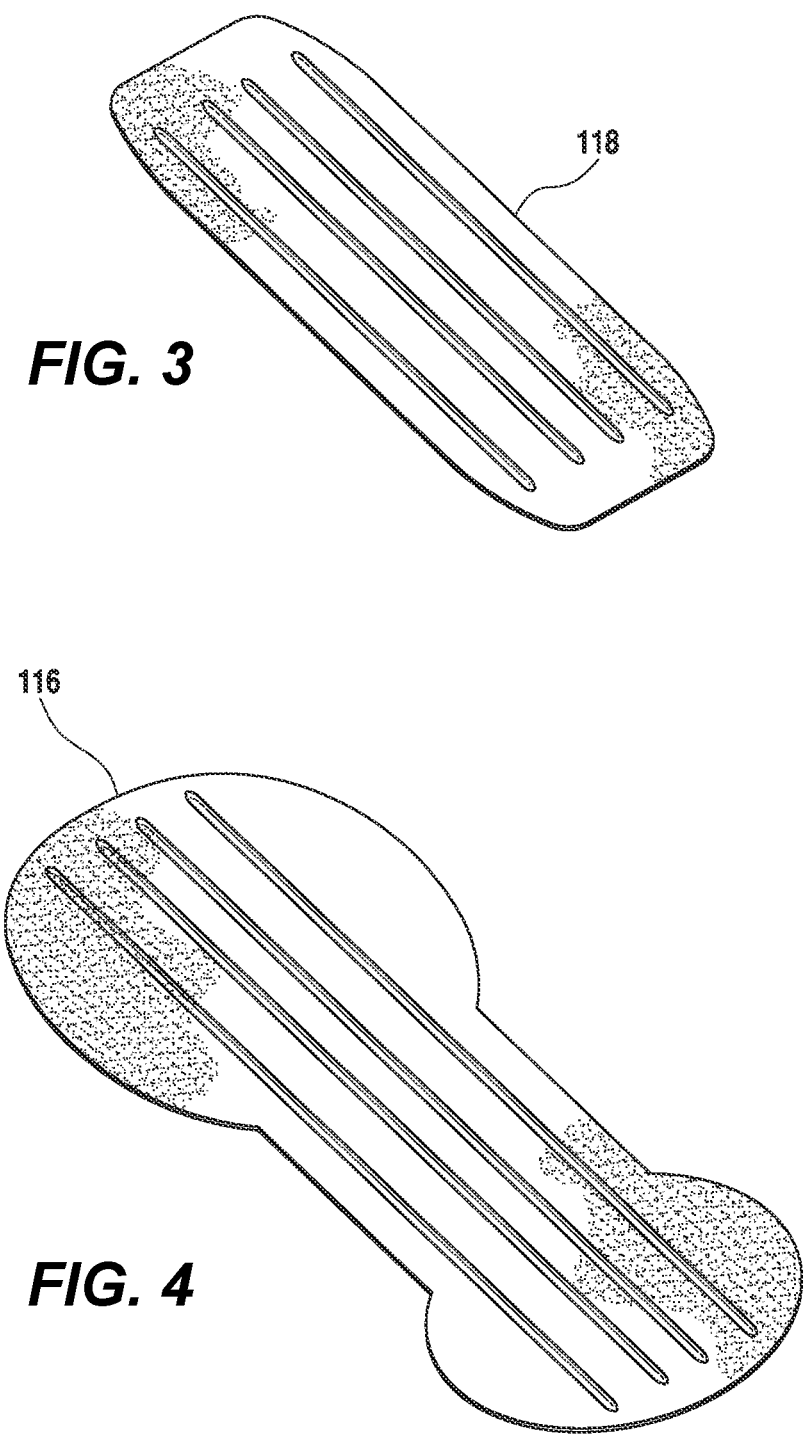
FIG. 3 is a perspective view of an absorbent core of the absorbent article depicted in FIG. 1.
FIG. 4 is a perspective view of a second absorbent core of the absorbent article depicted in FIG. 1.

FIG. 3 is a perspective view of a top (facing towards wearer) of the second core 118, and FIG. 4 is a perspective view of a bottom side (facing away from a wearer) of the first core 116. Each of the first core 116 and second core 118 can be composed of similar material, and can be shaped depending on the size of the absorbent article, and whether it is intended for use by infants, children and/or adults. By way of example, and as shown in FIGS. 3 and 4, first core 116 can be larger and substantially hourglass shaped, whereas second core 118 can be smaller, relative to first core 116, and can be substantially rectangular shaped. In this manner, the absorbent article can include a large surface area of coverage provided by the first core 116, and the increased absorbency provided by the second core 118, without the additional bulk of a second core having the same size as the first core.

First core 116 is shown having an embossed bottom and second core 118 is shown having an embossed top. The embossed top of second core 118 and the embossed bottom of first core 116 provide increased longitudinal flow while reducing lateral flow, and, in this manner, reducing leakage. Said another way, the embossed top of second core 118 and the embossed bottom of first core 116 allows fluid to move longitudinally towards the front and the back of a wearer, as opposed to towards the legs of a wearer.

Each of the first core 116 and the second core 118 may be composed of any materials suitable for absorbing the fluids and discharge including, but not limited to, a fibrous material (e.g., fluffed wood pulp), a super absorbent polymer ("SAP"), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper may vary depending upon whether it is intended for use by infants, children and/or adults.

While FIGS. 3 and 4 depict the first core 116 having an embossed bottom, and the second core 118 having an embossed top, in some embodiments, an absorbent article can have only a single core with no embossing, a single core with embossing on both, and/or other combinations of one or two cores each with embossing on one, both, or neither side. While the figures show absorbent articles include one or two cores, in some embodiments, absorbent articles can include more or fewer cores.

FIGS. 3 and 4 depict embossing as including four spaced apart embossing "lines," in some embodiments. However, a core can include more or fewer embossing lines. In some embodiments, embossing lines can be adjacent one another, or can be a combination of adjacent and space apart embossing line. In this manner, the different combinations of embossing lines can define an embossing pattern. While FIGS. 3 and 4 depict embossing substantially along the entire width and length of each respective core, in some embodiments a core can have embossing substantially along an entire width and/or length, and/or a portion of a width and/or length.

In embodiments of the invention, the first 116 and second 118 cores may be created with or without the use of super absorbent polymer (SAP). While some literature indicates that the presence of SAP in a diaper used for urine testing is considered benign, manufacturing diapers without SAP for the benefit of accuracy is contemplated by the present invention and may be considered beneficial.

Returning to FIGS. 1 and 2, the absorbent article 100 may further include a set of leak guards and/or a set of leg cuffs 142, 144, both known to those of ordinary skill in the art. Additionally, the exemplary absorbent article includes an outer layer or backsheet 135 and elastic bands 137. The elastic bands 137 can be used to gather the leg of the article around the user's leg, improving the fit of the absorbent article 100 and can improve the comfort of the wearer. Elastic bands and other elastic materials may be used at other places in the absorbent article in order to improve the fit and/or fluid retention of the article.

Figure 5:
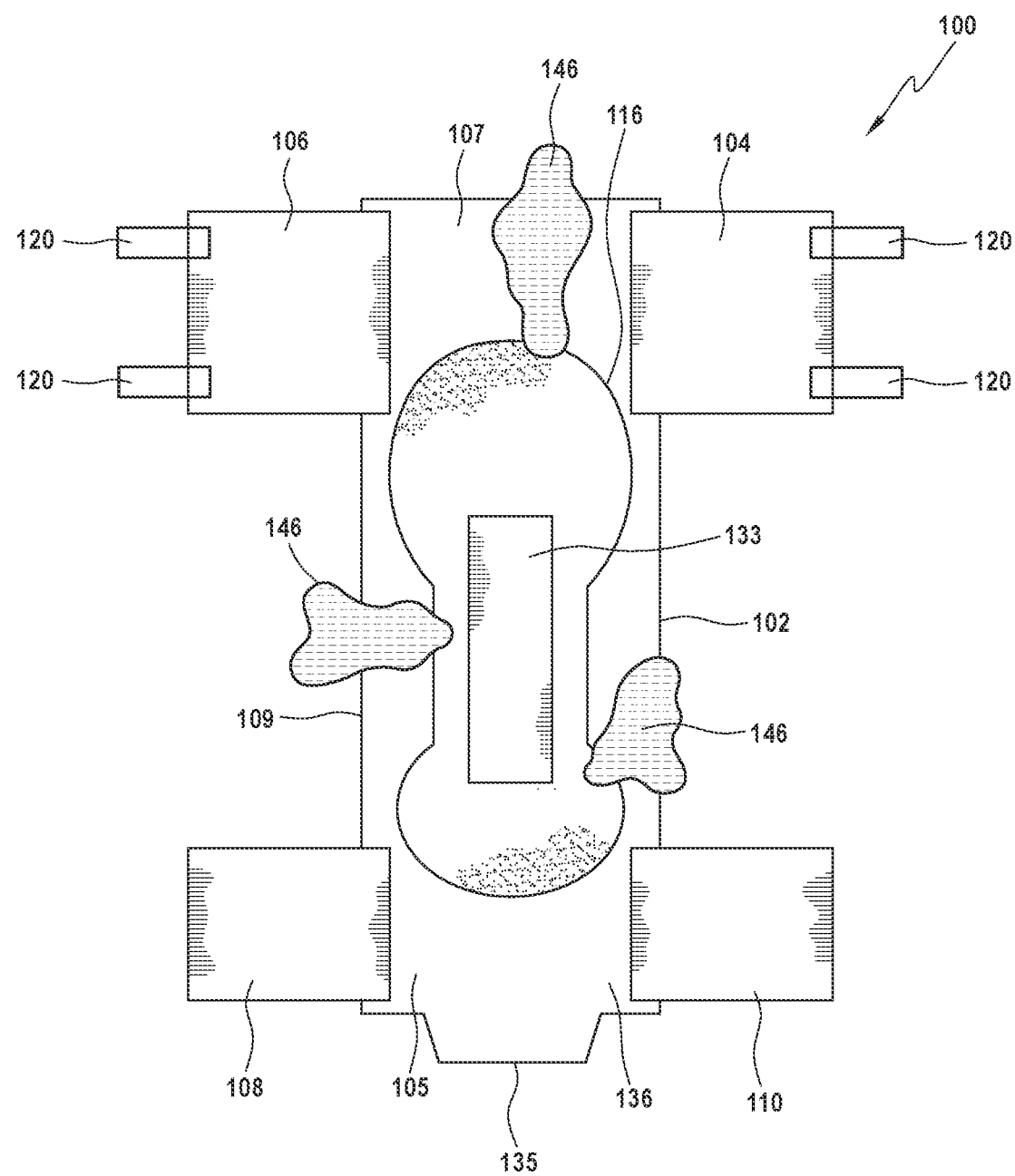
FIG. 5 is a top plan view of an absorbent article according to the prior art, similar to that of FIG. 1.

FIG. 5 illustrates the absorbent article 100 of FIG. 1 in which the absorbent layer 133 did not completely absorb the liquid and other discharge 146 deposited thereon. In this example, the liquid and other discharge 146 has moved to and beyond the outer edges of the chassis 102, and has leaked outside of the absorbent layer 133. As previously noted, such an instance is known to health and medical professionals, as well as to users of absorbent articles, as a blowout, which tend to occur when the absorbent layer 133 is abruptly overwhelmed by a large amount of liquid and other discharge 146 deposited onto it, resulting in the inability of the article to entirely absorb the waste. Such leaking may also occur as the result of an absorbent article that has been worn for too long, has built up too much waste, and can no longer absorb new waste.

Figure 6:
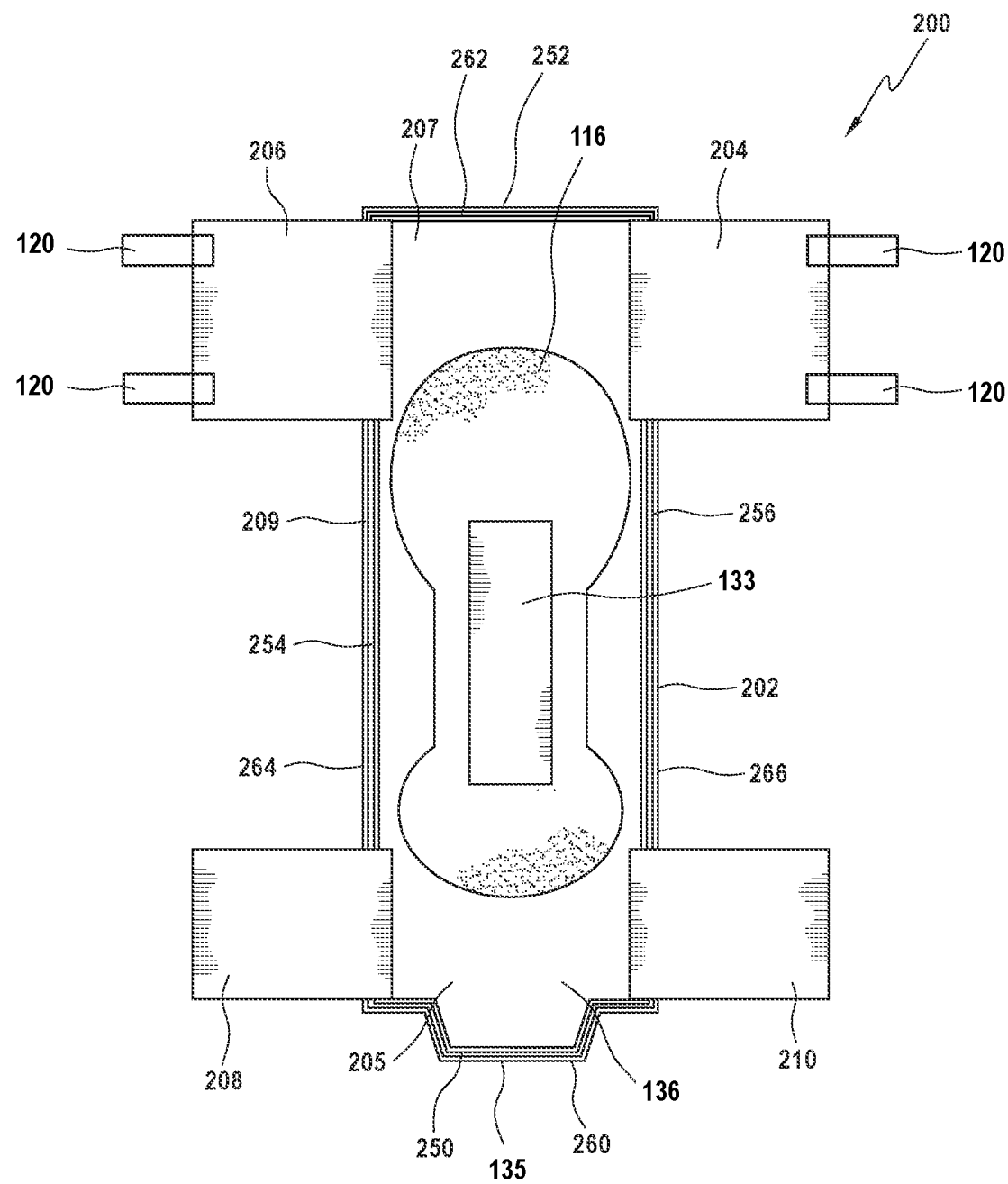
FIG. 6 is a top plan view of one embodiment of an absorbent article in a substantially flat un-contracted position according to one embodiment of the invention.
Figure 7:
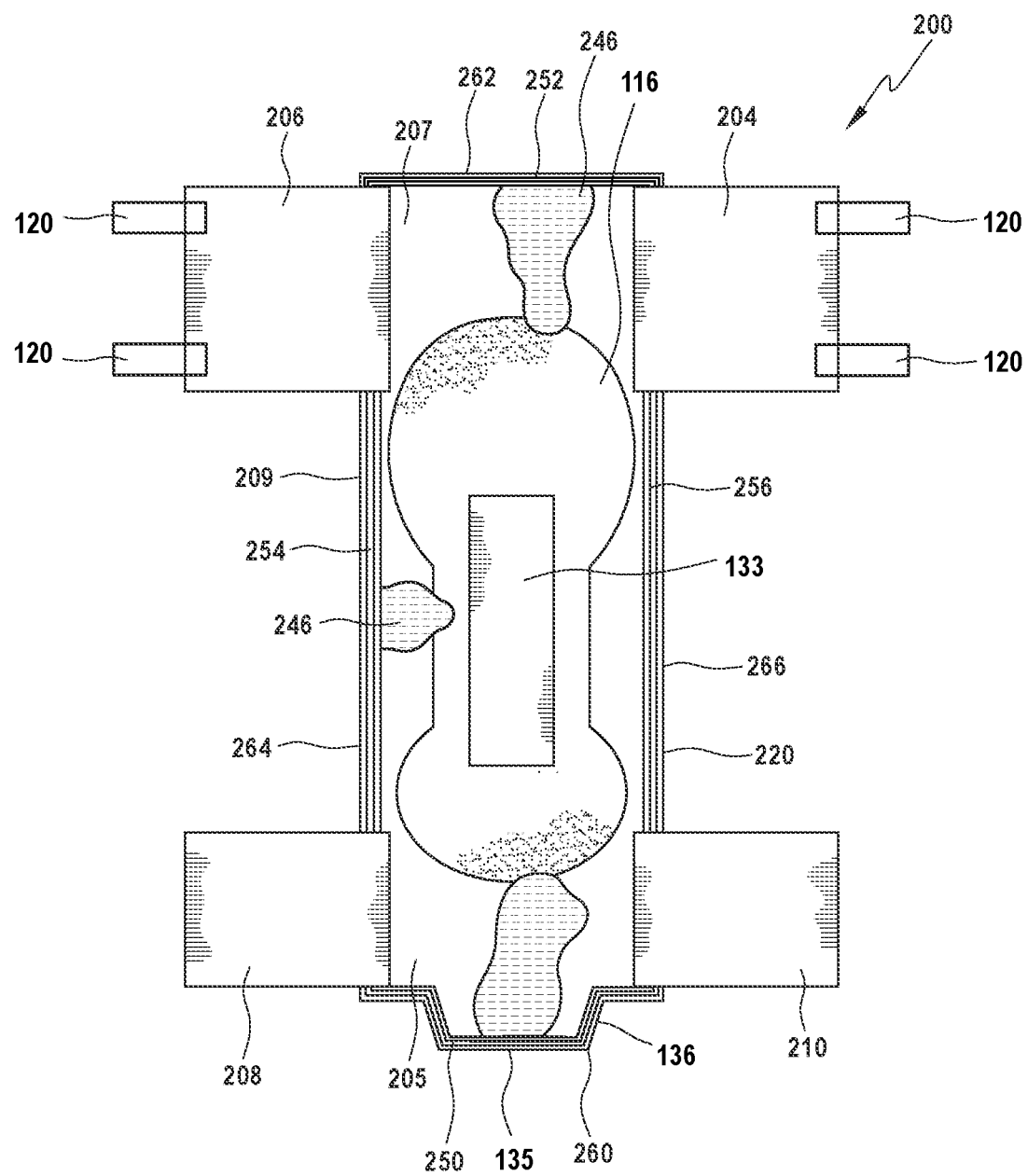
FIG. 7 is a top plan view of the absorbent article of FIG. 1, again in a substantially flat un-contracted position.

Referring now to FIGS. 6 and 7, the absorbent article 200 includes a chassis 202, similar to that of the embodiment of FIG. 1, and further comprises absorbent strips 250, 252, 254, 256 arranged at an outer edge 260 of the front waist region 205, an outer edge 262 of the back waist region 207, and at lateral edges 264, 266 of the crotch region 209. For the examples of FIGS. 6 and 7 the (130) topsheet has been removed to better illustrate the structure of the absorbent article 200. The absorbent strips are configured to absorb liquid and other discharge 246 that is initially deposited onto the absorbent layer 233 but that breaches that layer. It may be that the amount of waste 246 deposited onto the layer exceeds the amount that the absorbent layer 233 is capable of absorbing, or that the absorbent layer 233 cannot keep up with the rate at which the waste 246 is deposited onto the layer. When the liquid and other discharge 246 has overwhelmed the absorbent layer 233 and moved toward the outer edges 260, 262, 264, 266 of the chassis, the absorbent strips 250, 252, 254, 256 will act as an additional barrier, preventing the waste from leaking beyond the chassis outer edges.

FIG. 7 shows liquid and other discharge 246 that has breached the edges of the absorbent layer 233 and that has moved toward the outer edges of the chassis 102. However, unlike in the illustration of FIG. 5, once the excess waste 246 reaches the absorbent strips 250, 252, 254, 256 arranged at the edges 260, 262, 264, 266 of the front waist region 205, back waist region 207 and at lateral edges of the crotch region 309, it is absorbed by the absorbent strips and is prevented from breaching the outer edges of the chassis, stopping any potential leakage.

It will be understood by those of skill in the art that any number of absorbent strips could be placed at any number of the four edges 260, 262, 264, 266 of the absorbent article 200. It will also be understood that although one absorbent strip is demonstrated at each edge 260, 262, 264, 266, more than one absorbent strip could be placed at an edge to further assist in absorbing fluids. And though the absorbent strips demonstrated herein extend along the entire length of the outer edge to which they are arranged, it will be understood that the absorbent strips can be of any length, extending along the entirety of the edges or along only a portion of the edge.

The absorbent strips disclosed herein could comprise one, two or more layers of material depending on the level of absorbency desired. The absorbent strip could comprise a first and second core, similar to the first core 116 and second core 118 of FIGS. 3 and 4. Each core could have an embossed top or bottom to provide increased flow along the absorbent strip to further improve absorbency of greater amounts of liquid and other discharge, to assist in preventing leaking along the edges of the absorbent article.

In some embodiments, the absorbent strips could have a single core with no embossing, a single core with embossing on both sides, and/or other combinations of one or two cores each with embossing on one, both, or neither side. In some embodiments, an absorbent strip could include more or fewer cores.

The arrangement of embossing lines can differ in some embodiments. In some embodiments, embossing lines can be adjacent one another, or can be a combination of adjacent and spaced apart embossing line. In this manner, the different combinations of embossing lines can define an embossing pattern. The embossing could be substantially along the entire width and length of an absorbent strip, or it could be arranged along a portion of a width and/or length of the absorbent strip. Thus, an absorbent strip may extend along the entirety of an edge with embossing also extending along its entirety, or the absorbent strip may extend along a portion of the edge with the embossing extending along only a portion of the absorbent strip. Any combination of length and width of the absorbent strip with or without any combination of length or width of embossing is feasible.

The absorbent strips may be composed of any materials suitable for absorbing the fluids and discharge including, but not limited to, a fibrous material (e.g., fluffed wood pulp), a super absorbent polymer ("SAP"), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate (s) (e.g., methyl acrylate, ethyl acrylate, propyl acrylate, butyl acrylate, and hexyl acrylate). The absorbency of the diaper may vary depending upon whether it is intended for use by infants, children and/or adults. Preferably, the absorbent strips have a width of approximately 15 millimeters and a length substantially the length of the outer edge 260, 262, 264, 266 to which it corresponds.

Figure 8:
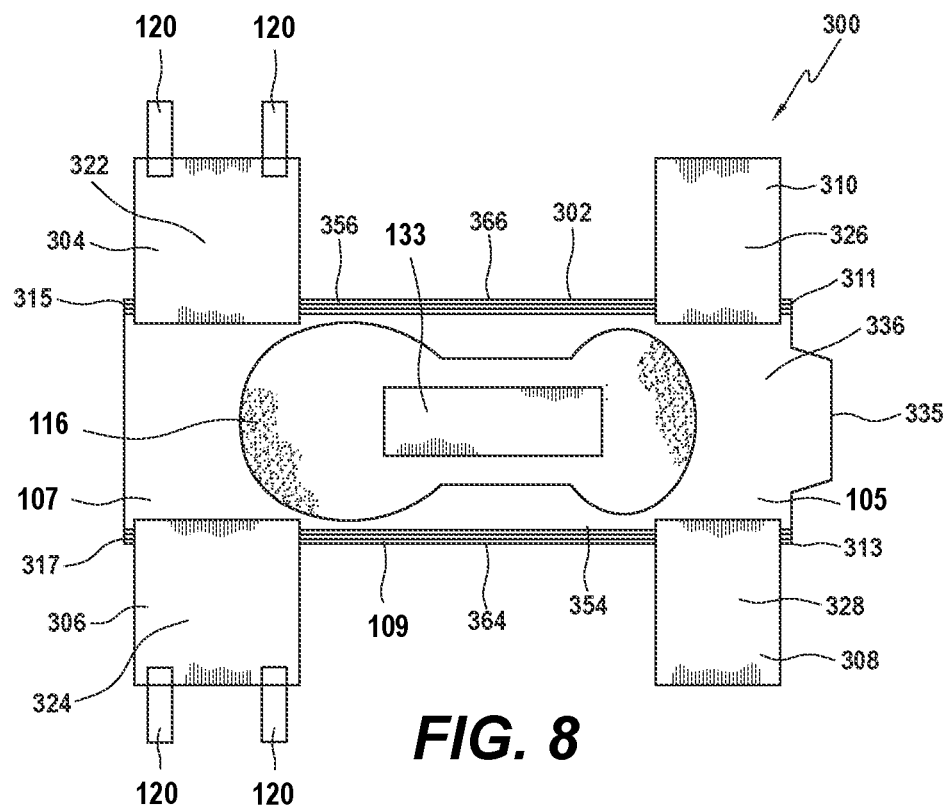
FIGS. 8 and 9 are top plan views of separate embodiments of an absorbent article in a substantially flat un-contracted position according to other embodiments of the invention.
Figure 9:
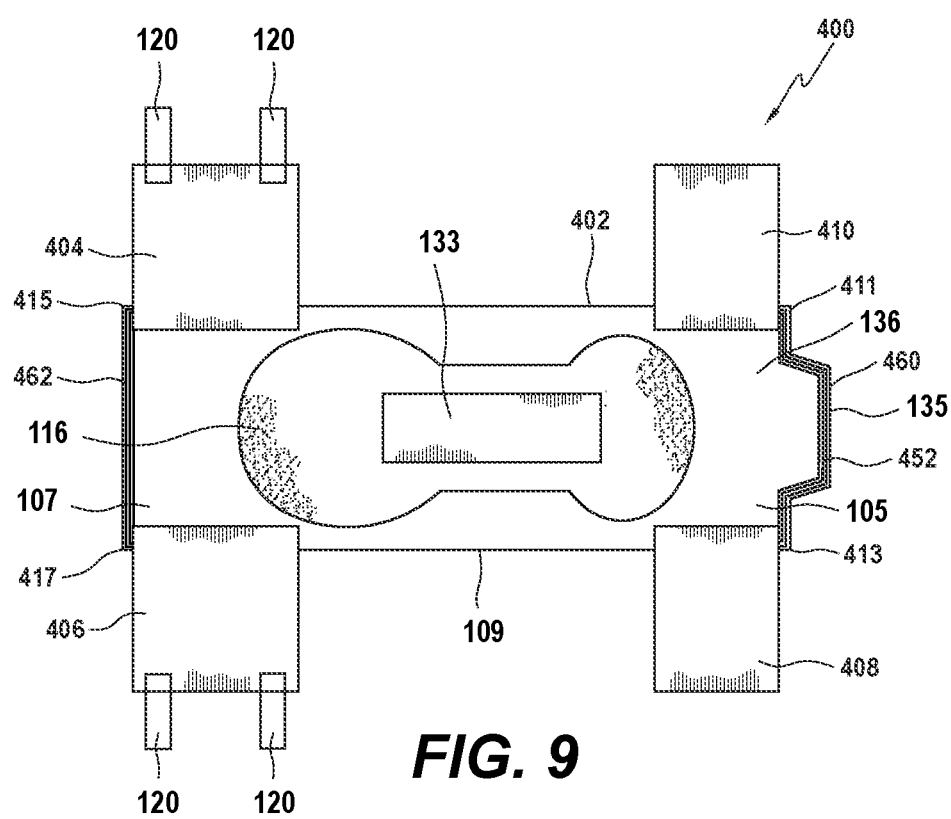

Referring now to FIGS. 8 and 9, additional embodiments of the absorbent article 300, 400 of the present disclosure are shown. Specifically, there is a chassis 302, 402 similar to that of FIGS. 1, 6 and 7 but including lateral edge absorbent strips 354, 356 arranged along the lateral edges 364, 366 of the crotch region 309 and/or longitudinal edge absorbent strips 450, 452 arranged at the edges 460, 462 of the front waist region 405 and back waist region 407, respectively. In the examples shown in FIGS. 8 and 9, the topsheet (130) has been removed to better illustrate the structure of the absorbent article 300, 400.

As illustrated in FIG. 8, lateral edge absorbent strips 354, 356 are positioned along the lateral edges 364, 366 of the absorbent article chassis 302. The exemplary strips extend continuously from front edges 311, 313 to a rear edge 315, 317. In this example, the strips extend across an outer surface of the side panels 304, 306, 308, 310 which are attached to an inner surface 336 of the backsheet 335. Alternatively, the side panels may be adhered to an outer surface of the backsheet 335 such that the lateral edge absorbent strips 354, 356 extend across an inner surface 322, 324, 326, 328 of the side panels 304, 306, 308, 310. In yet further embodiments, the absorbent strips may extend only along the chassis in a crotch portion 309 between the side panels 304, 306, 308, 310 such that the absorbent strips do not overlap with the side panels.

Illustrated in FIG. 9, longitudinal edge absorbent strips 450, 452 are positioned along the longitudinal edges 460, 462 of the absorbent article chassis 402. The exemplary strips extend continuously between front edges 411, 413 and between rear edges 415, 417. In this example the strips extend to an outer surface edge of the side panels 404, 406, 408, 410. Alternatively, the strips 450, 452 may extend along the inner surface edge of the side panels 404, 406, 408, 410, or may extend up to but not overlapping with the side panels.

Figure 10:
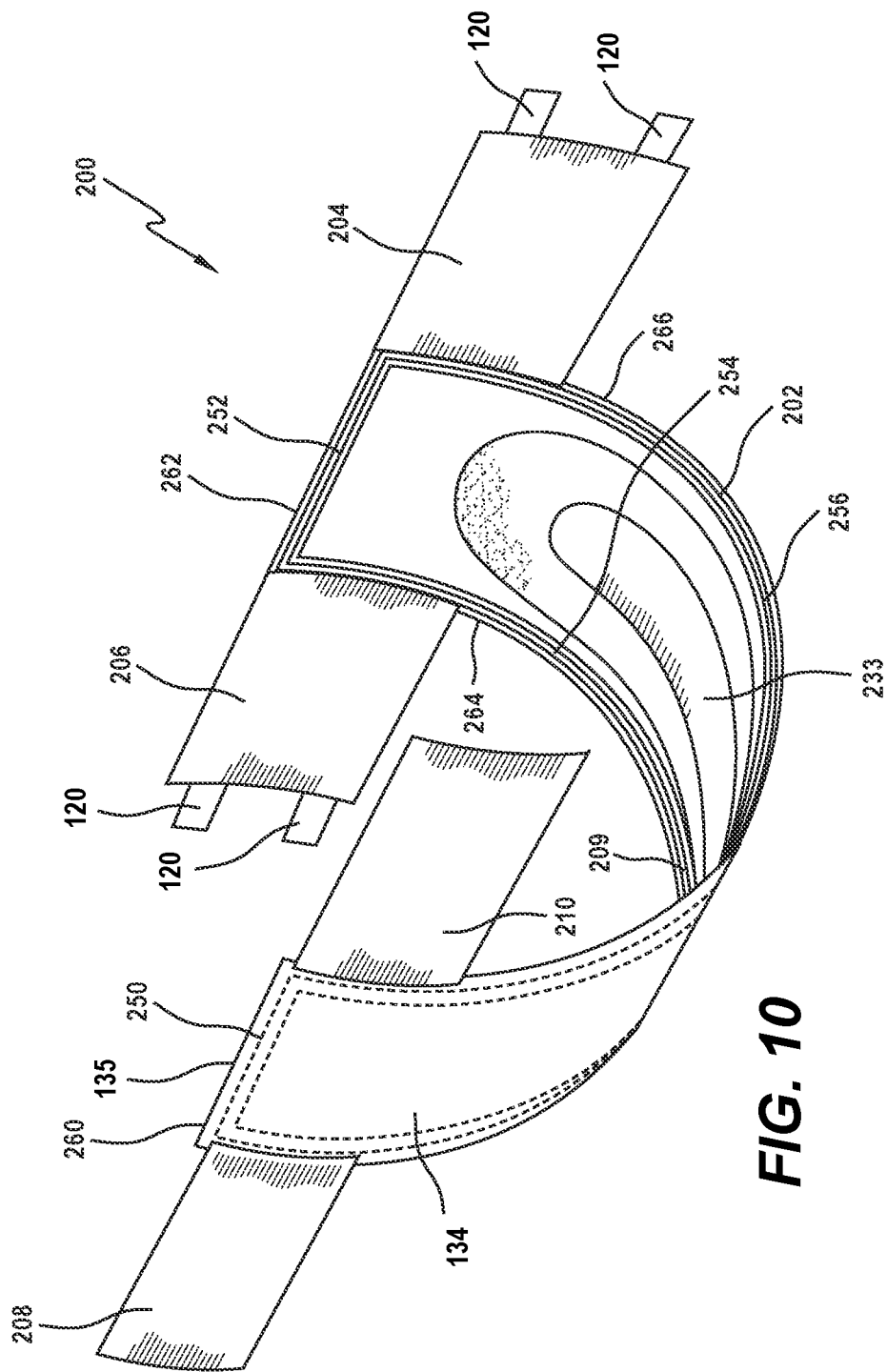
FIG. 10 is a perspective view of one embodiment of an absorbent article in a substantially rounded contracted position according to one embodiment of the invention.

FIG. 10 shows the embodiment of FIG. 6 but in a rounded, contracted state, as it would be formed when worn by a user. As is shown, the absorbent article 200 has absorbent strips 250, 252, 254, 256 arranged along the edges 260, 262, 264, 266 of the chassis, but it will be understood that, just as with FIGS. 8 and 9 as detailed above, the absorbent strips could be arranged at only the lateral edges 264, 266 or longitudinal edges 260, 262. In this example, the absorbent strips 250, 252, 254, 256 do not overlap with the side panels 204, 206, 208, 210 but rather are arranged adjacent to the panels. The absorbent strip could be arranged at a single edge of the chassis, rather than at more than one. Any number of strips placed at any of the chassis edges is considered by the invention.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. An absorbent article, comprising:
a chassis, the chassis having a length greater than its width, the length extending in a longitudinal direction from the back to the front of a user between first and second longitudinal edges and the width extending in a lateral direction substantially perpendicular to the length and between first and second lateral edges, the chassis comprising:
a liquid impervious backsheet,
a liquid pervious topsheet,
a front waist region,
a back waist region,
a crotch region, and
an absorbent core positioned in the crotch region between the backsheet and the topsheet; and
two elongated edge absorbent strips, each strip having a length greater than its width and comprising a fluid absorbent material;
wherein the absorbent strips are spaced apart from a perimeter of the chassis absorbent core; and
wherein the absorbent strips are adhered to the liquid impervious backsheet layer and covered by the liquid pervious topsheet layer;
wherein the absorbent strips comprise lateral edge absorbent strips arranged in parallel spaced relation to each other and proximate and parallel to each of the first and second lateral edges; and
wherein the lateral edge absorbent strips extend substantially the length of the chassis lateral edges.

2. The absorbent article of claim 1 further comprising two elongated longitudinal edge absorbent strips arranged in parallel spaced relation to each other and proximate and parallel to each of the first and second longitudinal edges.

3. The absorbent article of claim 2, wherein the elongated longitudinal edge absorbent strips extend in a direction that is generally normal to the lateral edge absorbent strips.

4. The absorbent article of claim 3, wherein the lateral edge absorbent strips and longitudinal edge absorbent strips surround substantially an entire perimeter of the chassis.

5. The absorbent article of claim 1, wherein the absorbent strips further comprise longitudinal edge absorbent strips arranged in parallel spaced relation to each other and proximate and parallel to each of the first and second longitudinal edges.

6. The absorbent article of claim 5, wherein the longitudinal edge absorbent strips extend substantially the length of the chassis longitudinal edges.

7. An absorbent article, comprising:
a chassis, the chassis having a length greater than its width, the length extending in a longitudinal direction from the back to the front of a user between first and second longitudinal edges and the width extending in a lateral direction substantially perpendicular to the length and between first and second lateral edges, the first and second lateral edges and first and second longitudinal edges forming a chassis perimeter, the chassis comprising:
a liquid impervious backsheet,
a liquid pervious topsheet,
a front waist region,
a back waist region,
a crotch region, and
an absorbent core positioned in the crotch region between the backsheet and the topsheet; and
an edge absorbent strip comprising one or more elongated strips, each elongated strip having a length greater than its width and comprising a fluid absorbent material;
wherein the edge absorbent strip is spaced apart from a perimeter of the absorbent core;
wherein the edge absorbent strip comprises one or more elongated lateral edge absorbent strips and one or more elongated longitudinal edge absorbent strips; and
wherein the edge absorbent strips surround substantially all of the chassis perimeter.

8. The absorbent article of claim 7, wherein the absorbent core comprises a substantially hourglass shape.

9. The absorbent article of claim 7 further comprising a side panel that extends beyond the chassis perimeter.

10. The absorbent article of claim 9, wherein the side panel does not overlap with the absorbent core.

11. The absorbent article of claim 10 wherein the side panel attaches to the chassis at a position that is interior of the edge absorbent strip.

12. The absorbent article of claim 10 wherein the side panel attaches to the chassis at a position that is exterior of the edge absorbent strip.

13. An absorbent article, comprising:
a chassis, the chassis having a length greater than its width, the length extending in a longitudinal direction from the back to the front of a user between first and second longitudinal edges and the width extending in a lateral direction substantially perpendicular to the length and between first and second lateral edges, the first and second lateral edges and first and second longitudinal edges forming a chassis perimeter, the chassis comprising:
a liquid impervious backsheet,
a liquid pervious topsheet,
a front waist region,
a back waist region,
a crotch region, and
an absorbent core positioned in the crotch region between the backsheet and the topsheet;
a front side panel extending from the first lateral edge in the front waist region;
a rear side panel extending from the first lateral edge in the back waist region; and
an elongated edge absorbent strip extending continuously at the first lateral edge from the front side panel to the rear side panel.

14. The absorbent article of claim 13, wherein the elongated edge absorbent strips each have a length greater than its width.

15. The absorbent article of claim 13, wherein the elongated edge absorbent strips each comprise a fluid absorbent material.

16. The absorbent article of claim 13, wherein the elongated edge absorbent strips each comprise a single absorbent layer.

* * * * *